US006755861B2

United States Patent
Nakao

(10) Patent No.: US 6,755,861 B2
(45) Date of Patent: Jun. 29, 2004

(54) DEVICE FOR PROVIDING A PORTION OF AN ORGANISM WITH A DESIRED SHAPE

(75) Inventor: Naomi Nakao, New York, NY (US)

(73) Assignee: Granit Medical Innovation, Inc., New York, NY (US)

( * ) Notice: Subject to any disclaimer, the term of this patent is extended or adjusted under 35 U.S.C. 154(b) by 11 days.

(21) Appl. No.: 09/978,414

(22) Filed: Oct. 16, 2001

(65) Prior Publication Data

US 2003/0074084 A1 Apr. 17, 2003

(51) Int. Cl.[7] .................................................. A61F 2/12
(52) U.S. Cl. ............................................. 623/8; 623/7
(58) Field of Search ............................. 623/7, 8, 1.25

(56) References Cited

U.S. PATENT DOCUMENTS

| | | | | |
|---|---|---|---|---|
| 4,507,810 A | * | 4/1985 | Bartholdson | 623/8 |
| 4,773,909 A | * | 9/1988 | Chaglassian | 623/8 |
| 5,496,367 A | * | 3/1996 | Fisher | 623/8 |
| 6,102,929 A | * | 8/2000 | Conway et al. | 606/192 |
| 6,187,043 B1 | * | 2/2001 | Ledergerber | 623/8 |
| 6,228,116 B1 | * | 5/2001 | Ledergerber | 623/8 |
| 6,508,756 B1 | * | 1/2003 | Kung et al. | 600/37 |

* cited by examiner

Primary Examiner—Corrine McDermott
Assistant Examiner—Kamrin Landrem
(74) Attorney, Agent, or Firm—R. Neil Sudol; Henry D. Coleman; William J. Sapone

(57) ABSTRACT

A method of breast reconstruction utilizes a breast prosthesis having a plurality of chambers or compartments distributed through a body member or shell in the form of a breast. The chambers are disposed along the superior, lateral and inferior surfaces, as well as in the interior, of the body member. The chambers are differentially pressurized or filled in order to control the shape of the prosthesis upon implantation thereof. Valves are provided for regulating the flow of fluid into and from the chambers. The prosthesis and the fill levels of the respective chambers may be selected by computer.

14 Claims, 3 Drawing Sheets

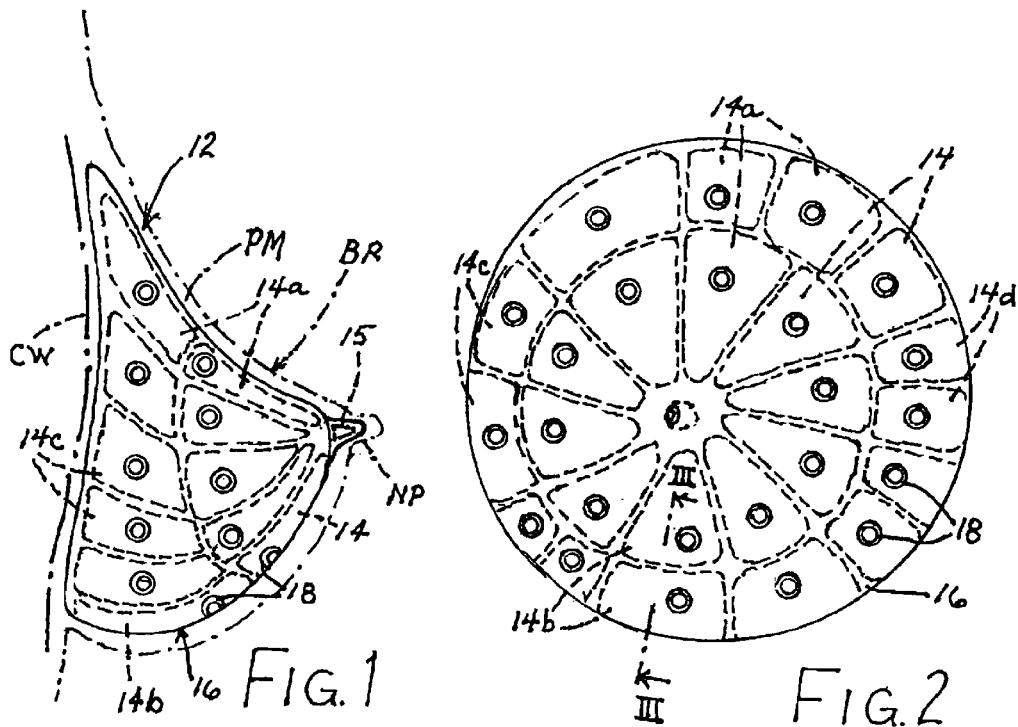
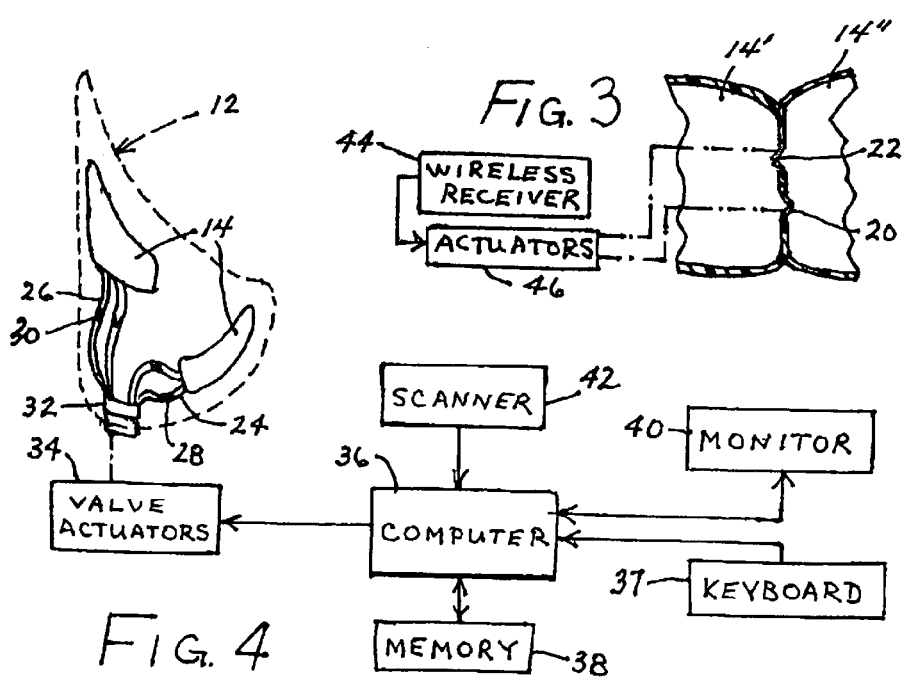

DEVICE FOR PROVIDING A PORTION OF AN ORGANISM WITH A DESIRED SHAPE

BACKGROUND OF THE INVENTION

This invention relates to a method for reshaping a portion of an organism through implantation of an expandable prosthesis. This invention also relates to the prosthesis. The invention is particularly suitable for providing a female breast with a desired shape.

It is not uncommon for women afflicted with breast cancer to have a breast removed in an attempt to prevent spread of a malignancy. Mastectomies are not just physically traumatic but also psychologically scarring. At the very least, women who have suffered mastectomies may lose their self confidence.

A number of methods for breast implants have been developed, but more often than not, the resulting breast has an unnatural appearance. When an implant alone is used, a silicone sack filled with saline is disposed beneath the pectoral muscle. Although this bag is usually shaped in the form of a breast, the saline acts in accordance with the laws of fluids and distributes itself in the shape of least resistance so that the middle of the bag assumes a spherical shape. The lateral aspect of this prosthetic breast, where breast tissue is supposed to exist, is now empty. The resulting unnatural appearance is that of a ball placed beneath the skin rather than the tear-drop shape of a natural breast, with the sloping of the superior part of the breast, the even tapering distribution laterally and the droop on the inferior side.

OBJECTS OF THE INVENTION

It is an object of the present invention to provide a method and/or an associated prosthetic device for reconstructing and shaping a body part.

A more specific object of the present invention is to provide such a method and/or device for reconstructing and shaping a breast.

Another object of the present invention is to provide such a method and/or device which facilitates the fashioning of a natural breast shape.

It is a further object of the present invention to provide such a method and/or device which includes computer aided design.

These and other objects of the present invention will be apparent from the drawings and descriptions hereof. It is to be noted that every embodiment of the invention is expected to achieve one of more of these objects. However, no embodiment is expected to achieve all objects of the invention.

SUMMARY OF THE INVENTION

The present invention is directed in part to a method of breast reconstruction utilizing a breast prosthesis having a plurality of chambers or compartments distributed through a body member or shell in the form of a breast. The chambers are disposed along the superior, lateral and inferior surfaces, as well as in the interior, of the body member. The chambers are differentially pressurized in order to control the shape of the prosthesis upon implantation thereof. Chambers on the superior side of the body member are underpressurized or underfilled to result in a desired sloping aspect, whereas chambers on the inferior side are filled to a greater degree to provide a rounded full aspect. Chambers on the outer lateral side of the body member of the prosthesis are filled to intermediate levels to provide a gently rounded aspect, while chambers on the inner lateral side of the body member may be filled to a lower intermediate fill ratio to provide a more tapering aspect to that side of the reconfigured breast.

The present invention contemplates that the compartments or chambers of the prosthesis have shapes, sizes, and relative positions which facilitate the formation, after differential filling or pressurization of the chambers, of a reconstructed breast of a desired shape. The chamber configuration may vary among a number of different breast prostheses designed for generating breasts of different sizes and shapes.

Generally, a prosthesis in accordance with the present invention comprises a body member made of biocompatible material and having a plurality of inflatable chambers. Fluid guide elements are operatively connected to respective chambers for enabling a differential pressurization of the chambers with a fluid. The fluid is typically a saline solution but may take the form of any biocompatible fluid.

The guide elements may include a plurality of one-way valves each disposed between two adjacent chambers for enabling a transfer of fluid from one of the adjacent chambers to another upon an application of an external compressive force to the one adjacent chambers. Thus, the valves enable a reshaping of the breast merely through manipulation. Alternatively, non-invasive sculpting of the breast may be achieved by remote control where a signal receiver is embedded on or attached to the prosthesis, together with actuators for automatically opening and closing the valves in accordance with instructions received via the signal receiver. The signal receiver may be a wireless receiver which picks up radio-frequency electromagnetic signals or ultrasonic pressure wave signals.

The fluid guide elements may alternatively include a plurality of conduits connected to and communicating with respective ones of the chambers. The conduits may be provided with one-way valves for regulating the flow of fluid through the conduits. In that case, each chamber may be provided with a pair of conduits for alternatively delivering and removing fluid from the chamber.

In accordance with another feature of the present invention, the conduits may be connected also to at least one terminal connector or holder mounted to the body member. The terminal connector may be provided with indicators for identifying which chambers are connected to which conduit terminals. The indicators may consist of color coding or other marking scheme. Thus, by a simple visual inspection, a physician or other medical practitioner can easily locate a terminal for delivery of fluid to (or removal of fluid from) a desired chamber of the prosthesis.

In a particular configuration of the body member of the prosthesis, the valves are located at the ends of the conduits, in or proximate to the terminal connector on the body member of the prosthesis. The valves may then be operated manually.

In another mode of filling the chambers, an actuator mechanism is releasably coupled to the conduits and valves via the connector. In that case, the valves may be automatically operated by the actuator mechanism under the control of a computer to introduce fluid into the different chambers of the prosthesis in predetermined amounts. The amounts of fluid may be established by selecting one of a plurality of predetermined breast shapes, the fluid amounts being previously stored in a memory of the computer. Alternatively, the amounts of fluid may be calculated by the computer upon selecting of a breast shape.

A breast shape may be selected by several methods. For instance, where shapes are stored as electronic templates in a library of the computer's memory, selection occurs upon viewing the different stored shapes on a computer monitor. For providing a better idea of the possible overall results, the various shapes from the library may be paired with an image (e.g., body-type silhouette or digitized photograph) of the woman undergoing breast reconstruction. Alternatively, a scanner may be used to digitally record the shape of her actual breast prior to removal thereof during surgery. The computer may then analyze the digitized shape and select a suitable prosthesis configuration and a set of fluid levels for the various chambers of the selected prosthesis, to most closely reproduce the recorded breast shape and size. The computer may be programmed to select or fine-tune the fluid levels in the different chambers of a selected prosthesis in order to most closely approximate the size and shape of the breast prior to surgery. Where a breast has already been removed by surgery, the other breast of the woman may serve as a template for selecting a prosthesis and pressure or fluid levels.

In accordance with another feature of the present invention, the guide elements of the prosthesis include a plurality of radio-opaque markers (e.g., rings) disposed on the body member adjacent to respective chambers for facilitating a selection of needle insertion points for the respective chambers. The markers thus serve to guide the hand of the physician, for instance, plastic surgeon or cosmetologist, during a fluid injection phase of a breast reconstruction procedure. It is well known that breast reconstruction requires several temporally spaced steps of incrementally increasing the amount of fluid in an implanted prosthesis, thus enabling a gradual stretching of the pectoral muscle. For this reason, the guide elements are helpful for facilitating repeated introduction of fluid to periodically elevate the fill levels in the compartments or chambers.

A method for reshaping a portion of an organism utilizes, in accordance with the present invention, a body member made of biocompatible material, the body member having a plurality of inflatable chambers. The method comprises implanting the body member into a patient in a pre-established location, selecting a desired shape of the portion of the organism, and differentially expanding the chambers with a fluid to respective fill levels to at least approximate the desired shape.

As discussed above, the selecting of the desired shape may include scanning a part of the organism to generate a digitized representation of the desired shape and loading the digitized representation into an electronic memory. The fill levels for the respective chamber are selected to generate the desired shape, this selection process including automatically analyzing the digitized representation to compute the fill levels.

Scanning of the body part may be achieved by any suitable technique, particularly by devices which generate digital representations of two- or three-dimensional forms. Useful scanning technologies include flying spot scanning, optical imaging by digital cameras, ultrasonic scanning, laser scanning, and mechanical sensing. In addition, cameras sensitive to electromagnetic wavelengths other than optical may be useful, for instance, those operating on infrared frequencies. Laser scanning takes surface slices of an object, based on distance from the laser. These slices are then reconstructed into a three-dimensional surface. This technique has been used in the film industry to scan an actor's body into an electronic database for purposes of generating a three-dimensional animated image.

Where a human breast is to be reconstructed, for instance, following a mastectomy, the scanned body part is either the breast to be removed or, alternatively, the other breast of the patient. In the former case, the breast with the cancer or other degenerative disease has not substantially lost its original healthy shape at the time the decision is made to resect the breast. In the latter case, the mastectomy may have already occurred or the breast may have otherwise been altered from its natural form. The electronic three-dimensional image of the healthy breast is processed to undergo a mirror-image conversion to produce an electronic facsimile of the removed or diseased breast.

It is to be noted that all of the above-mentioned scanning techniques may be used either directly on the body part being scanned or indirectly, for instance, on a casting of the body part. More specifically, a mold may be made of the body part. The mold may be fabricated by placing plaster-soaked fabric on the body part, with the plaster being permitted to harden to form a mold. In any event, the electronic surface or contour data may be generated by scanning the inner surface of the mold or by scanning an exterior surface of a casting made via the mold.

As further discussed above, the selecting of the desired shape alternatively includes storing a library of possible shapes of the portion of the organism in an electronic memory, selecting a plurality of the possible shapes, generating on an image reproduction device a plurality of images each corresponding to a respective one of the selected possible shapes, and thereafter selecting one of the plurality of the possible shapes as the desired shape. In addition, a plurality of target fill levels for respective chambers of a prosthesis may be stored in the memory, for each of the possible shapes. Then, the selecting of the fill levels for the respective chambers includes automatically selecting the target fill levels corresponding to or associated with the desired shape in the memory.

Where the body member is provided with a plurality of conduits extending to respective chambers from a terminal connector on the body member, the differential expanding of the chambers may include coupling an inflation or fluid delivery connector to the terminal connector.

Where the body member is provided with a plurality of markers disposed adjacent to respective chambers, the expanding of the chambers includes scanning the patient to detect the markers, inserting a hollow needle into the chambers at respective locations indicated by the markers, and introducing a pressurization fluid into the chambers through the inserted needle.

BRIEF DESCRIPTION OF THE DRAWINGS

FIG. 1 is a schematic side elevational view of a breast prosthesis in accordance with the present invention.

FIG. 2 is a schematic front elevational view of the prosthesis of FIG. 1.

FIG. 3 is a schematic partial cross-sectional view taken along line III—III in FIG. 2.

FIG. 4 is partially a block diagram and partially a partial schematic exploded view of another breast prosthesis in accordance with the present invention.

DETAILED DESCRIPTION OF THE PREFERRED EMBODIMENTS

Figure 5:
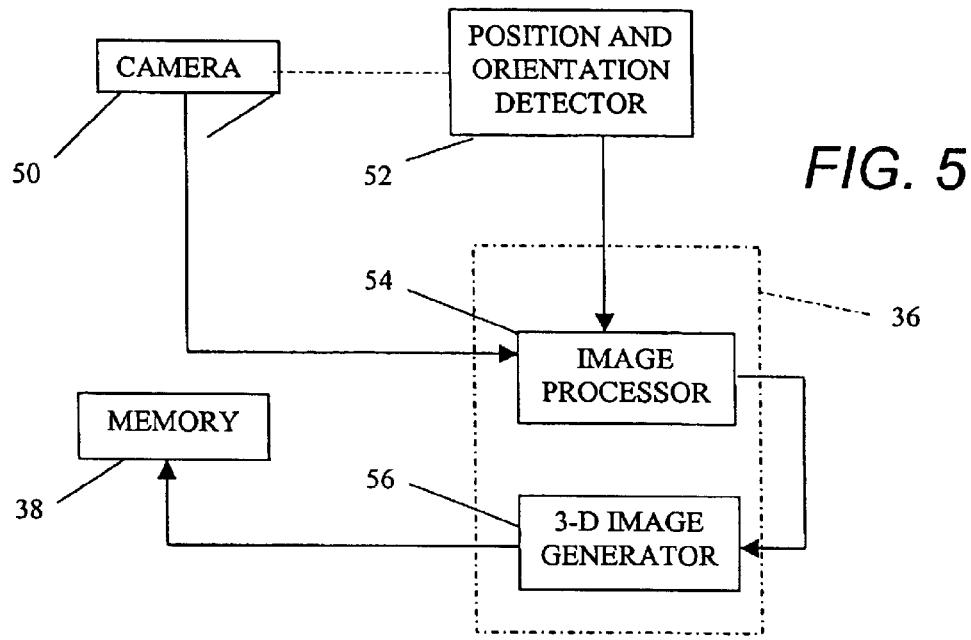
FIG. 5 is a block diagram showing a particular embodiment of a scanner illustrated in FIG. 4 and components of a computer therein.

As illustrated in FIGS. 1 and 2, a breast prosthesis 12 has a plurality of chambers or compartments 14 distributed through a body member or shell 16 in the general form of a human breast. Chambers 14 have shapes, sizes, and relative positions which facilitate the formation, after a differential filling or pressurization of the chambers, of a reconstructed breast BR of a desired shape. A number of different breast prostheses may be provided with respective chamber distributions and configurations for reproducing breasts of different sizes and shapes.

In a breast reconstruction procedure, the prosthesis 12 is implanted in a deflated configuration between a chest wall CW and pectoral muscles PM. In this deflated configuration, chambers 14 are essentially empty. The prosthesis 12 may be sutured to the chest wall CW at several locations to hold the implant in place relative to the chest wall CW. Special areas may be provided on body member or shell 16 for suturing so that none of the chambers 14 are punctured.

After implantation of prosthesis 12, a pressurization or filling fluid such as a saline solution is introduced into the chambers 14. Subsequently, the saline solution in the chambers 14 may be periodically augmented after the pectoral muscles PM have had an opportunity to stretch in response to the incrementally expanded volume beneath the muscles. Ultimately, in a final shape or configuration of prosthesis 12, chambers 14 are filled with fluid to respective fill levels to approximate a desired breast shape.

Chambers 14 include upper chambers 14a disposed along a superior side (not separately designated) of the prosthesis 12, lower chambers 14b disposed along inferior surfaces of prosthesis 12, as well as chambers 14c and 14d disposed along an outer lateral side and an inner lateral side of body member 16. Chambers 14a, 14b, 14c, 14d are differentially filled in order to control the shape of the prosthesis 12 upon implantation thereof. Upper chambers 14a are underpressurized or underfilled to result in a ski-slope-type aspect, whereas lower chambers 14b are substantially filled to provide a rounded full aspect. Lateral chambers 14c are filled to intermediate levels to provide a gently rounded aspect, while chambers 14d may be filled to a lower intermediate fill ratio to provide a more tapering aspect to that side of the reconfigured breast.

Prosthesis 12 may include a special compartment 15 formed at a tip of the breast mound to create a nipple form NP. This reconstructed nipple NP with an elevated extension at the tip can simulate the original nipple and be placed between the pectoral muscle PM and the skin (not separately desiganted). The skin may be tattooed in the area of the nipple implant compartment 15 to provide the color of a nipple.

Body member or shell 16 is made of biocompatible material and is formed with a plurality of fluid guide elements operatively connected to respective chambers 14 for enabling a differential pressurization of the chambers 14 with a fluid. These fluid guide elements may take the form of radio-opaque marker rings 18 disposed on body member 16 adjacent to respective chambers 14 for guiding or directing a plastic surgeon in the selection of needle insertion points for the respective chambers 14. In order to inject the filling fluid into a chamber 14, the surgeon or physician inserts a hypodermic needle (not shown) through the respective ring 18 under radiographic guidance. The amount of fluid injected at any particular time depends in large part on the resilience of the pectoral muscles PM and the desired ultimate breast shape and size. The amount of fluid in any particular chamber 14 may be reduced by inserting a hypodermic needle under radiographic guidance and sucking fluid through the needle. Special channels (not shown) may be provided through or between chambers 14a, 14b, 14c, 14d to inner chambers, should they exist in the interior of the prosthesis.

As illustrated in FIG. 3, the fluid guide elements associated with chambers 14 may also include one-way valves 20 and 22 each disposed between two adjacent chambers 14' and 14". Valve 20 guides fluid from chamber 14' to chamber 14" upon the manual application of a compressive force to chamber 14'. Similarly, valve 22 permits a transfer of fluid in the opposite direction, from chamber 14" to chamber 14' upon the manual application of a compressive force to chamber 14". Thus, valves 20 and 22 enable a reshaping of the breast BR through simple manipulation, without invasive action.

In an alternative embodiment depicted in FIG. 4, the fluid guide elements associated with chambers 14 include a plurality of inlet conduits 24 and a like plurality of outlet conduits 26 connected to and communicating with respective chambers 14. Conduits 24 are provided with respective one-way valves 28 for selectively enabling the injection of fluid into chambers 14, for instance, when the pressure on the upstream sides of the valves 28 exceed the pressures of the fluid in the respective chambers 14. Likewise, conduits 26 are provided with respective one-way valves 30 for selectively enabling the removal of fluid from chambers 14, when the pressure in the chambers exceed the pressures of the fluid on the downstream or outlet sides of the valves 30.

Conduits 24 and 26 may be connected also to at least one terminal connector or holder 32 mounted to body member 16, for instance, along the underside of prosthesis 12. Terminal connector 32 may be provided with color-coding or other indicators for identifying which chambers 14 are connected to which conduit 26. Thus, by a simple visual inspection, a plastic surgeon or other medical practitioner can easily locate a terminal for delivery of fluid to a desired chamber 14 of the prosthesis 12. The injection of fluid may be accomplished by inserting a needle into the selected conduit 26. Valves 28 may take the form of self-sealing membranes disposed at the outer ends of conduits 26, for instance, at terminal connector 32, for facilitating an insertion of a needle tip through the valves 28.

In another mode of filling the chambers 14 in the embodiment of FIG. 4, an actuator mechanism 34 is releasably coupled to the conduits 24 and 26 and valves 28 and 30 via the connector 32. In that case, valves 28 and 30 may be automatically operated by the actuator mechanism 34 under the control of a computer 36 to introduce controlled amounts of fluid into the different chambers 14 of prosthesis 12. During intermediate stages of breast reconfiguration, the amounts of fluid introduced into chambers 14 depend on the extent to which the pectoral muscles PM and the patient's own sense of comfort can accommodate increased fluid amounts. These variables may be monitored by the attending physician, with instructions being supplied to computer 36 via a keyboard 37 or other user input device. Alternatively, the tension on the pectoral muscles PM may be monitored by a sensor.

A breast shape may be selected by any of several alternative methods. For instance, where shapes are stored as electronic templates in a library of a memory 38 of computer 36, selection is made by the patient in consultation with her physician upon viewing different stored shapes displayed on a monitor 40 by computer 36 in accordance with the information stored in memory 38, For providing a better idea of the possible overall results, the various shapes from the library may be paired with or superimposed on an image (e.g., body-type silhouette or digitized photograph) of the patient. Alternatively, a scanner 42 may be used to digitally record the shape of the patient's actual breast prior to ressection thereof. Scanner 42 is operatively connected to computer 36 for feeding thereto a digitized image or images of the breast to be reconstructed. A three-dimensional electronic model of the breast may be constructed by computer 36 from a series of two-dimensional images.

Computer 36 may be programmed to analyze the digitized shape and select, from memory 38, a suitable configuration of a prosthesis 12 and a set of final fluid levels for the various chambers 14 of the selected prosthesis, to most closely reproduce the recorded breast shape and size. Computer 36 may be further programmed to select or fine-tune the fluid levels in the different chambers 14 of a selected prosthesis 12 in order to most closely approximate the size and shape of the breast prior to surgery. Where a breast has already been removed by surgery, the contralateral breast of the patient may serve as a template for selecting a prosthesis 12 and ultimate pressure or fluid levels in chambers 14.

In a modified process, computer 36 may be programmed to calculate, based on a selected breast shape and size, the final or ultimate amounts of fluid to be introduced in chambers 14.

Of course, more complicated forms are chamber pressurization control are possible. For instance, in an automatic control system, a plurality of gravity switches or acceleration sensors may be provided in body member 16 of prosthesis 12 for sensing the inclination of the user's chest. The sensors are connected to a microprocessor controller (not shown) for interpreting the sensor signals to determine modifications to the pressure levels or fill levels in the compartments or chambers 14 to reshape the breast prosthesis 12 depending on whether the user is upright, lying prone on her back, lying on her side, etc. In this version of the prosthesis, valves 20 and 22 disposed between the various chambers 14 may be actuated by the microprocessor to enable a redistribution of the saline levels depending on the posture of the user.

In another variation, the user may more actively vary her breast shape. An input device (not shown) may be connected to a microprocessor controller (not shown) disposed in the prosthesis 12 or elsewhere in or on the person of the user. The user may instruct the microprocessor to vary the breast shape and size depending on the social or physical circumstances in which the user is engaged. A formal evening affair, for example, might call for a larger breast size than an afternoon exercise session.

In yet another variation of the breast prosthesis 12, valves 20 and 22 provided between the various adjacent pairs of chambers 14' and 14" may be actuatable via an electrical or magnetic signal. Such as signal may be transmitted through implanted wiring (not shown) or wirelessly to a radio-frequency electromagnetic-wave receiver 44 connected to actuators or servomechanisms 46 for operating valves 20 and 22, receiver 44 and actuators 46 being disposed in the prosthesis. Alternatively, control may be effectuated through pressure wave signals. In this embodiment, a first series of pulses may open a particular valve, while another series of pulses closes the valve. The pulses are typically ultrasonic and have low amplitudes or energy.

Computer 36 may be programmed to depict the various chambers 14 of prosthesis 12 on monitor 38 in association with identification codes such as alphanumeric designations. For instance, if a user would like to address a section B (not shown) which is situated at 6 o'clock of the breast and extends to 7 o'clock towards the nipple NP, one would be able to find section B on the remote control.

As depicted in FIG. 5, scanner 42 may take the form of a camera 50, preferably a digital camera, which is sensitive to optical and/or infrared wavelengths. The orientation and position of camera 50 is tracked by a set of detectors 52 which provide signal output to computer 36 and more particularly to an image processor module 54 thereof. This position and orientation date is used by image processor 54 in coordinating different views of a breast or other organic body part taken by camera 50. Image processor 54 performs preliminary processing of image data from camera 54 and provides the processed image data to a three-dimensional image generator 56 which is also a module of computer 36. Image generator 56 constructs an electronic model of the three-dimensional body part or other structure which is scanned by camera 54. The three-dimensional model is stored in memory 38.

Figure 6:
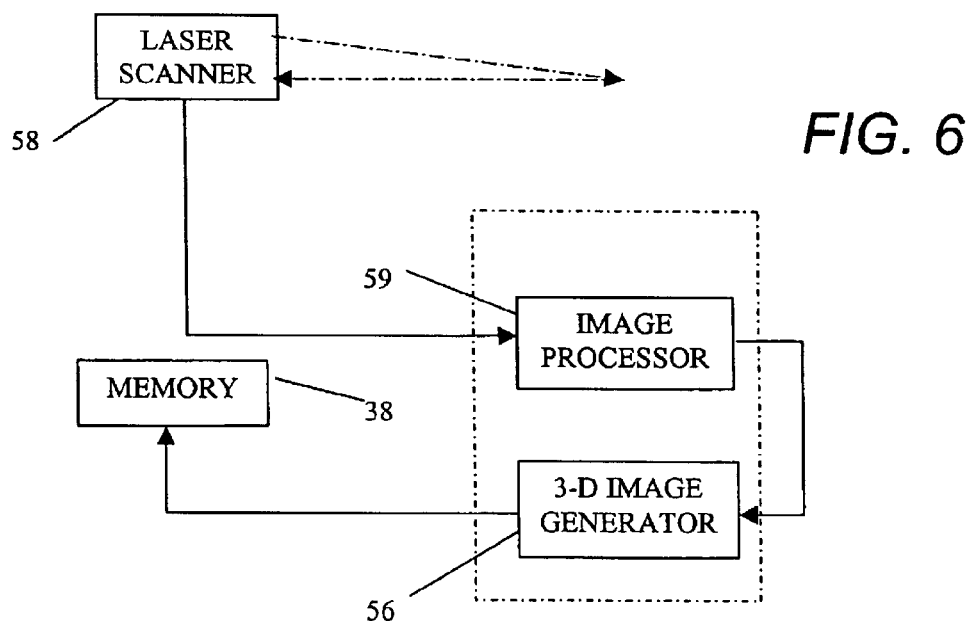
FIG. 6 is a block diagram similar to FIG. 5, showing another particular embodiment of the scanner of FIG. 4.

As illustrated in FIG. 6, scanner 42 (FIG. 4) may take the specific form of a laser scanner 58. Laser scanner 58 operates in accordance with known principles to map an exterior surface of a body part such as a breast by scanning successive planar contours or slices of the body part. This method is used in the movie industry to detect and encode three-dimensional structures such as human forms for loading thereof into an electronic database for use as animation material. However, any kind of laser scanning technique may be used, including interferometric methods, flying spot scanners, distance measurement processes, etc. Laser scanner 58 is operatively connected to a data preprocessor 59 and 3-D image generator 56.

Figure 7:
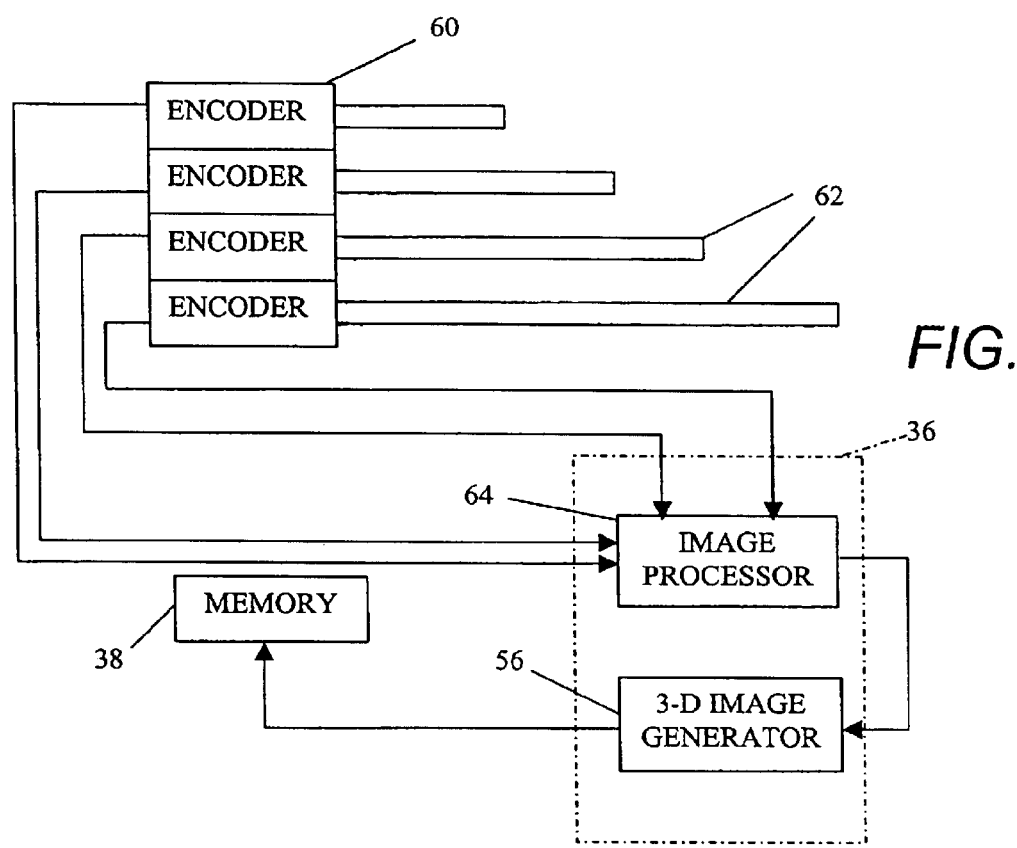
FIG. 7 is a block diagram similar to FIGS. 5 and 6, showing yet another particular embodiment of the scanner of FIG. 4.

As shown in FIG. 7, scanner 42 (FIG. 4) may take a mechanical form incorporating, for instance, a multiplicity of mechanoelectric transducers or encoders 60 arranged in a linear or planar array and provided with respective extendible sensor elements 62 such as telescoping tongues. Encoders 60 are electrically connected to a data preprocessor 64 in turn connected to 3-D image generator 56.

It is to be noted that the procedures and devices described herein may be utilized to provide breast augmentation for women who have not had a mastectomy but merely wish to increase their breast size.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A breast prosthesis comprising:

a body member made of biocompatible material, said body member having a plurality of separately inflatable chambers, said body member having an upper side positionable along an upper surface of a breast and a lower side positionable along a lower side of the breast, said chambers including a first chamber disposed only on said upper side and a second chamber disposed only on said lower side; and a plurality of fluid guide elements, wherein the fluid guide elements comprise a plurality of one-way valves each operatively connected to a respective individual ones of said chambers for enabling a differential filling of said chambers with a fluid so that said first chamber and said second have respective different shapes.

2. The prosthesis set forth in claim 1 wherein said guide elements include a plurality of conduits each connected to and communicating with a respective individual ones of said chambers.

3. The prosthesis set forth in claim 2 wherein said guide elements also comprise at least one terminal connector mounted to said body member and coupled with at least a plurality of said conduits.

4. The prosthesis set forth in claim 1 wherein said guide elements include a plurality of radio-opaque markers each disposed on said body member adjacent to a respective individual ones of said chambers for enabling a detection of needle insertion points for said chambers.

5. The prosthesis set forth in claim 4 wherein said markers are rings.

6. The prosthesis set forth in claim 1 wherein said plurality of one-way valves each disposed between two adjacent chambers for enabling a transfer of fluid from one of said adjacent chambers to another of said adjacent chambers, further comprising a receiver and an actuator mechanism mounted to said body member, said actuator mechanism being operatively linked to said receiver and said valves for selectively opening said valves in accordance with a signal picked up by said receiver.

7. The prosthesis set forth in claim 6 wherein said receiver is a wireless receiver and said signal is a wirelessly transmitted signal.

8. The prosthesis set forth in claim 1 wherein said prosthesis has a form suitable for simulating the shape and size of a human breast, said first side being suitable for an upper side of the breast and said second side being suitable for a lower side of the breast.

9. The prosthesis set forth in claim 1 wherein said plurality of one-way valves each disposed between two adjacent chambers for enabling a transfer of fluid from one of said adjacent chambers to another of said adjacent chambers upon an application of an external compressive force to said one of said adjacent chambers, to increase a fill level in said one of said chambers.

10. A prosthesis comprising:
a body member made of biocompatible material, said body member having a plurality of separately inflatable chambers;
a plurality of fluid guide elements each operatively connected to a respective individual one of said chambers, thereby enabling a differential filling of said chambers with a fluid; and
a plurality of one-way valves each disposed between two adjacent chambers for enabling a transfer of fluid from one of said adjacent chambers to another of said adjacent chambers upon an application of an external compressive force to said one of said adjacent chambers, to increase a fill level in said one of said chambers.

11. The prosthesis set forth in claim 10 wherein said guide elements include a plurality of conduits each connected to and communicating with a respective individual one of said chambers.

12. The prosthesis set forth in claim 11 wherein said guide elements additionally comprise a plurality of one-way valves each disposed in communication with a respective individual one of said conduits.

13. The prosthesis set forth in claim 10, further comprising a receiver and an actuator mechanism mounted to said body member, said actuator mechanism being operatively linked to said receiver and said valves for selectively opening said valves in accordance with a signal picked up by said receiver.

14. A prosthesis comprising:
a body member made of biocompatible material, said body member having a plurality of separately inflatable chambers;
a plurality of fluid guide elements each operatively connected to a respective individual one of said chambers, thereby enabling a differential filling of said chambers with a fluid, said guide elements including a plurality of valves;
a wireless receiver; and
an actuator mechanism mounted to said body member, said actuator mechanism being operatively linked to said receiver and said guide elements for selectively opening said valves in accordance with a signal picked up by said receiver.

* * * * *

UNITED STATES PATENT AND TRADEMARK OFFICE
CERTIFICATE OF CORRECTION

PATENT NO. : 6,755,861 B2
DATED : June 29, 2004
INVENTOR(S) : Naomi L. Nakao

It is certified that error appears in the above-identified patent and that said Letters Patent is hereby corrected as shown below:

<u>Title page,</u>
Item [73], Assignee, should read -- Granit Medical Innovation LLC, New York, NY (US) --

Signed and Sealed this

Ninth Day of August, 2005

JON W. DUDAS
*Director of the United States Patent and Trademark Office*